United States Patent [19]
Lew

[11] Patent Number: 5,121,658

[45] Date of Patent: * Jun. 16, 1992

[54] MASS-VOLUME FLOWMETER

[76] Inventor: Hyok S. Lew, 7890 Oak St., Arvada, Colo. 80005

[*] Notice: The portion of the term of this patent subsequent to Jul. 17, 2007 has been disclaimed.

[21] Appl. No.: 368,406

[22] Filed: Jun. 19, 1989

Related U.S. Application Data

[63] Continuation-in-part of Ser. No. 208,739, Jun. 20, 1988, Pat. No. 4,941,361.

[51] Int. Cl.⁵ .............................................. G01F 1/32
[52] U.S. Cl. ..................................... 73/195; 73/861.22
[58] Field of Search ............... 73/197, 203, 861.02, 73/861.03, 861.22, 861.24, 195

[56] References Cited

U.S. PATENT DOCUMENTS

| | | | |
|---|---|---|---|
| 3,719,073 | 3/1973 | Mahon | 73/861.22 |
| 3,776,033 | 12/1973 | Herzl | 73/861.22 |
| 4,010,645 | 3/1977 | Herzl | 73/861.22 |
| 4,048,854 | 9/1977 | Herzl | 73/861.04 |
| 4,523,477 | 6/1985 | Miller | 73/861.22 |

FOREIGN PATENT DOCUMENTS 5548612  4/1980 Japan .......................................... 73/195

Primary Examiner—Herbert Goldstein

[57] ABSTRACT

A flowmeter measuring mass flow rate or volume flow rate or mass and volume flow rates of fluid comprises a pair of flow passages (3 and 4) and a pair of flow sensors (7 and 8) respectively measuring flow rates through the two flow passages (3 and 4). A flow obstructing member (12) at least partially obstructs at least one of the two flow passages (3 and 4), wherein a bias force acting on the flow obstructing member (12) tends to increase the degree of obstruction of the fluid flow through said at least one of the two flow passages, while the fluid dynamic force exerted on the flow obstructing member (12) by the fluid moving through the flowmeter tends to decrease the degree of obstruction of the fluid flow through said at least one of the two flow passages. The mass flow rate of the fluid moving through the flowmeter is determined as a function of the signals provided by the pair of flow sensors (7 and 8), and the volume flow rate of the fluid moving through the flowmeter is determined as another function of the signals provided by the pair of flow sensors (7 and 8). The density of the fluid is determined as a ratio of the mass flow rate to the volume flow rate.

18 Claims, 4 Drawing Sheets

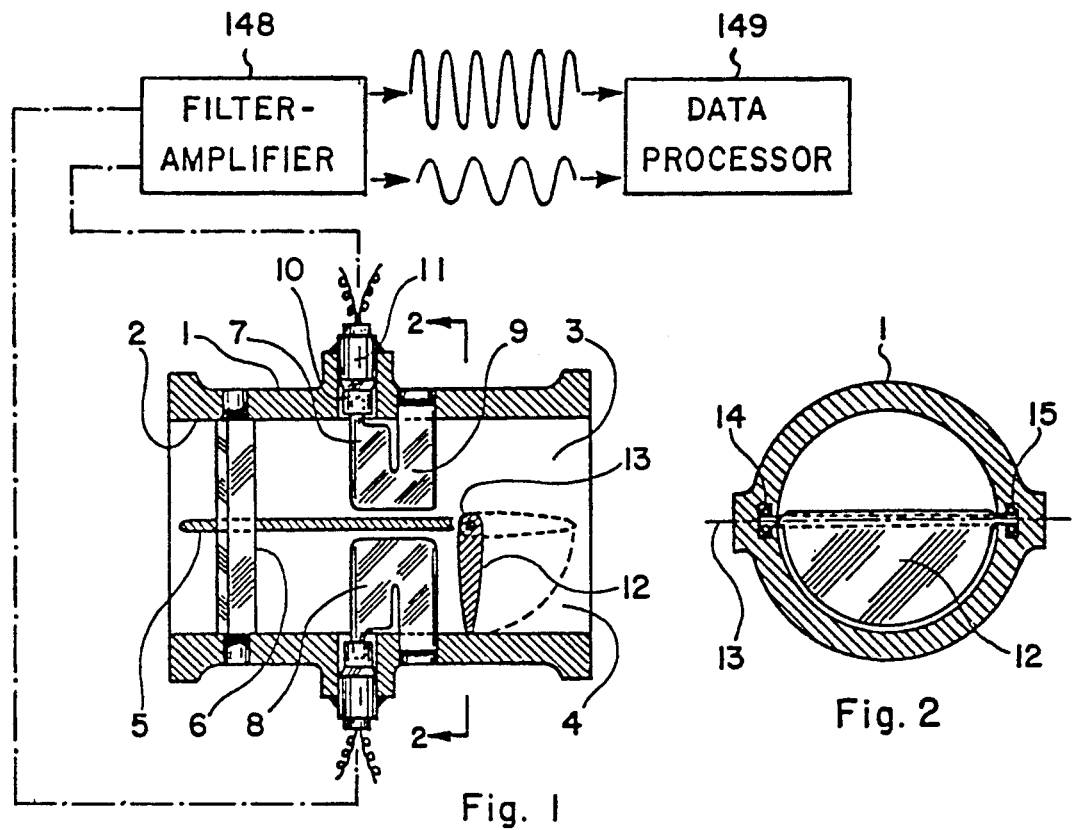
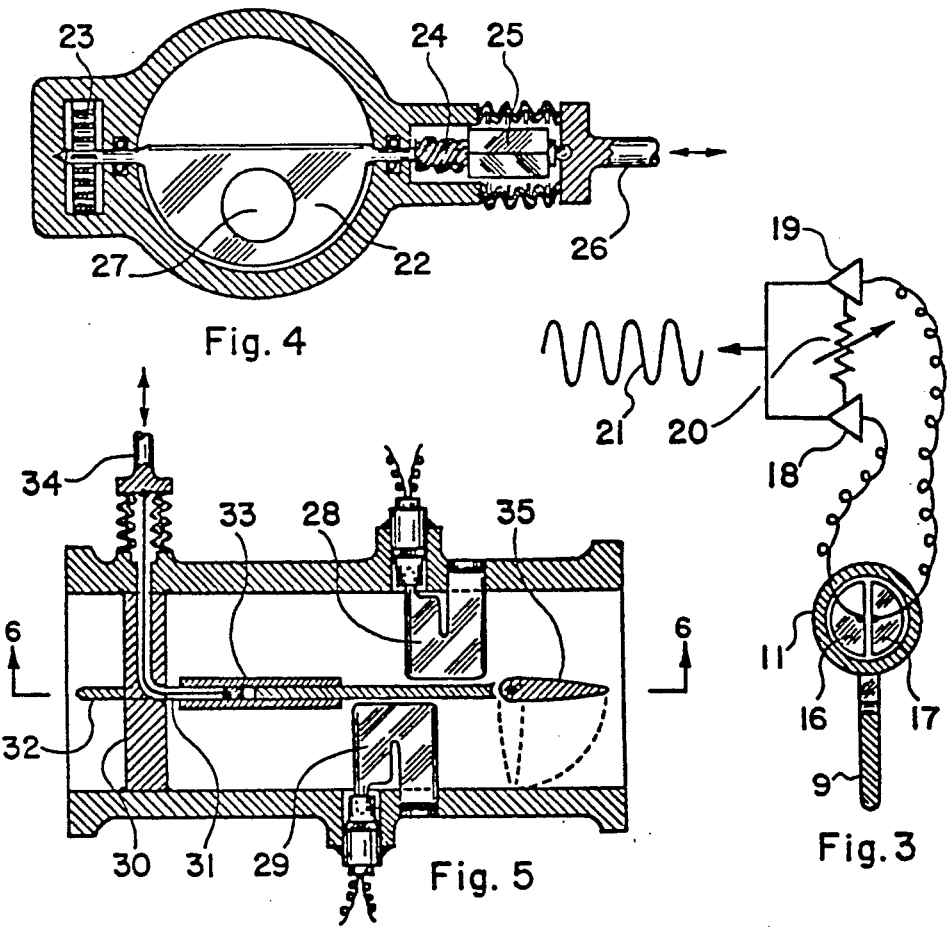

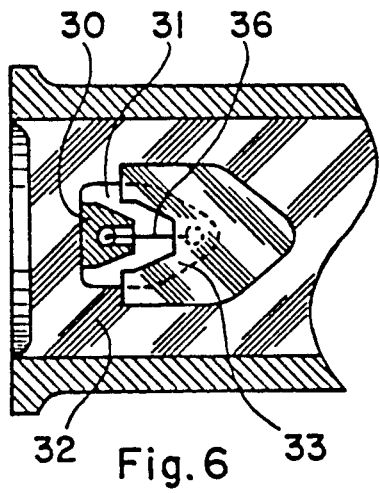
Fig. 6
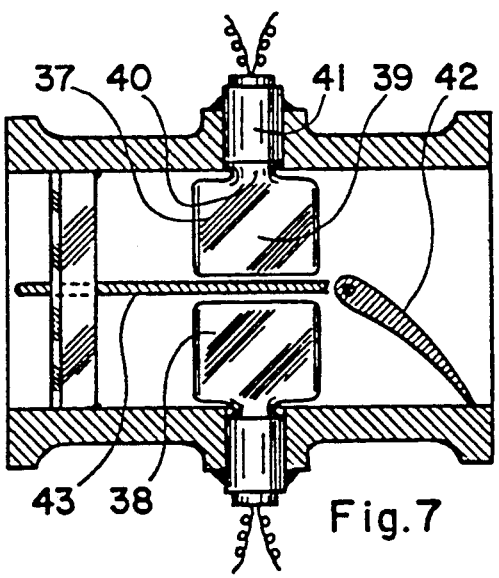
Fig. 7
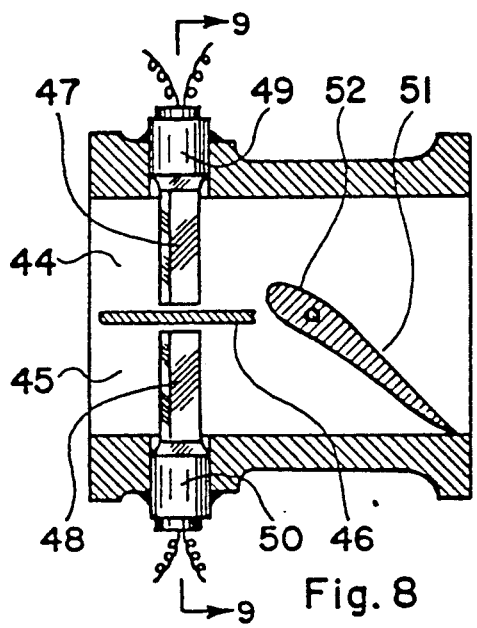
Fig. 8
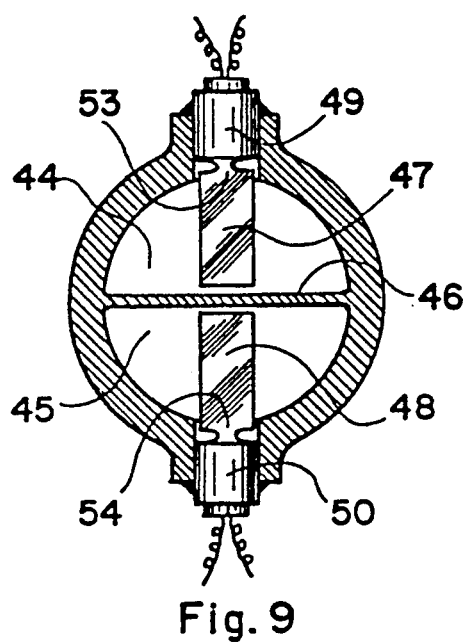
Fig. 9
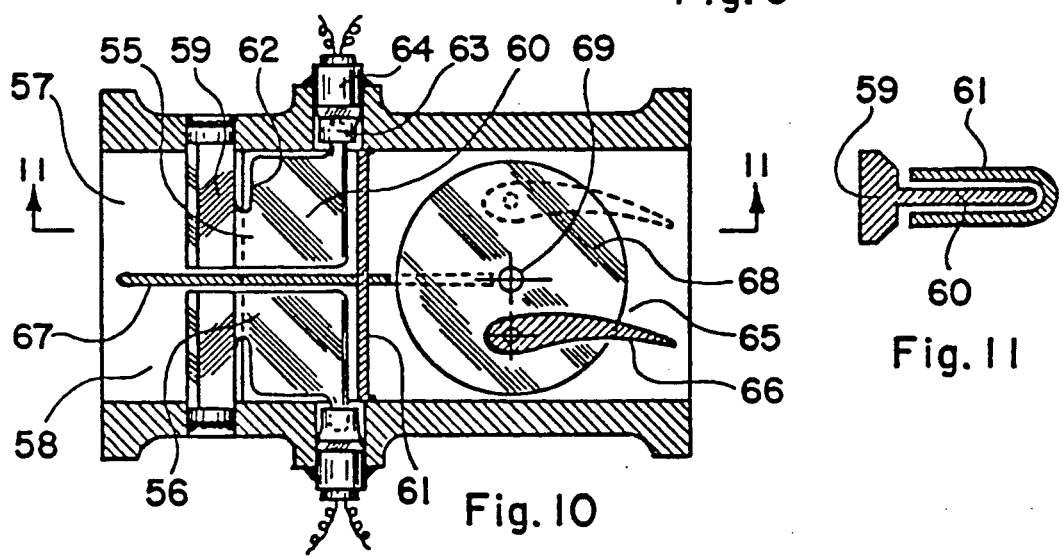
Fig. 10
Fig. 11

MASS-VOLUME FLOWMETER

The priority of the invention described and claimed in this patent application is based on parent U.S. patent application Ser. No. 07/208,739 entitled "Three-In-One Flowmeter" filed on Jun. 20, 1988 that is now U.S. Pat. No. 4,941,361, to which this patent application is a continuation-in-part.

The flowmeter of the present invention comprises two flow passages respectively including a pair of flow sensors for measuring volume flow rates or mass flow rates of a fluid moving through each of two flow passages, wherein at least one of the two flow passages includes a flow obstructing member that obstructs the fluid flow through one of the two flow passages in varying degrees as a function of the mass flow rate through the flowmeter, wherein the degree of the obstruction of the flow by the obstructing member decreases as the fluid dynamic force on the flow obstructing member increases, which fluid dynamic force increases as the flow rate of the fluid increases. When the pair of flow sensors included in the flowmeter are the type of sensors measuring volume flow rate, the volume flow rate through the flowmeter is determined from an additive combination of the outputs from the two flow sensors, while the mass flow rate is determined by combining the volume flow rate and a differential combination of the output from the two flow sensors. When the pair of the flow sensors included in the flowmeter are the type of sensors measuring mass flow rate, the mass flow rate through the flowmeter is determined from an additive combination of the outputs from the two flow sensors, while the volume flow rate is determined by combining the mass flow rate and a differential combination of the two outputs from the flow sensors. Of course, the fluid density may be obtained as the ratio of the mass flow rate to the volume flow rate.

All of the flowmeters available at the present time measure mass flow rate or volume flow rate, but none of the present day flowmeters meters are capable of measuring both the mass flow rate and volume flow rate. The mass-volume flowmeter capable of simultaneously measuring the mass flow rate and the volume flow rate will bring forth a breakthrough in the flow measuring technology for the following reasons: Firstly, the existing mass flow measuring technologies fail to provide accuracy and reliability in measuring many types of multiphase flow and, more particularly, mixtures of liquid and gaseous media such as wet steam and foamy materials, which types of materials are very extensively involved in today's industrial as well as domestic fluid handling and controlling processes. Secondly, there are many volume flow sensors available today, which volume flow sensors are far more reliable or versatile compared with the mass flow measuring sensors in many applications. Consequently, technology providing a mass flow measuring capability to a flowmeter employing volume flow sensors will promote accuracy and versatility in the mass flow measuring technologies to a level comparable to that in the volume flow measuring technologies.

The primary object of the present invention is to provide a mass-volume flowmeter comprising two flow passages respectively including a pair of flow sensors, wherein at least one of the two flow passages includes a flow obstructing element obstructing the fluid flow through one of the two flow passages, which flow obstructing member progressively opens up or closes down the one of the two flow passages as the fluid dynamic force exerted thereon by the fluid moving through the two flow passages increases or decrease. The volume flow rate of fluid moving through the flowmeter is determined as a function of the outputs from the pair of the flow sensors, while the mass flow rate is determined as another function of the outputs from the pair of the flow sensors. The density of the fluid may be determined as the ratio of the mass flow arte to the volume flow rate.

Another object is to provide a mass-volume flowmeter wherein the flow obstructing element includes a spring bias that counter-acts the fluid dynamic force thereon exerted by the fluid moving through the mass-volume flowmeter.

A further object is to provide a mass-volume flowmeter wherein the flow obstructing element includes an earth's gravitational force bias that counter-acts the fluid dynamic force thereon.

Yet another object is to provide a mass-volume flowmeter including an over-riding mechanism that either fully opens or fully closes the flow obstructing member.

Yet a further object is to provide a mass-volume flowmeter wherein the pair of the flow sensors included therein comprises a pair of volume flow measuring sensors.

Still another object is to provide a mass-volume flowmeter wherein the pair of the flow sensors included therein comprises a pair of mass flow measuring sensors.

Still a further object is to provide a mass-volume flowmeter including a pair of vortex sensors wherein the fluid velocity is determined either from the vortex shedding frequencies detected by the pair of vortex sensors or from the difference in time of travel from a common vortex generator to the pair of vortex sensors respectively located at two different downstream locations from the vortex generator.

These and other objects of the present invention will become clear as the description thereof progresses. The present invention may be described with a great clarity and specificity by referring to the following figures:

FIG. 1 illustrates a cross section of an embodiment of the mass-volume flowmeter comprising a vortex generator and a pair of vortex sensors respectively disposed in two flow passages inlcuded in the flowmeter.

FIG. 2 illustrates another cross section of the embodiment shown in FIG. 1.

FIG. 3 illustrates a Piezo electric transducer and diagram of the electrical signal flow therefrom, which combination is employed in the vortex sensor.

FIG. 4 illustrates an alternative arrangement of the embodiment shown in FIG. 2.

FIG. 5 illustrates a cross section of another embodiment of the mass-volume flowmeter comprising a vortex generator and a pair of vortex sensors.

FIG. 6 illustrates another cross section of the embodiment shown in FIG. 5.

FIG. 7 illustrates a cross section of a further embodiment of the mass-volume flowmeter including a vortex generator and a pair of vortex sensors.

FIG. 8 illustrates a cross section of an embodiment of the mass-volume flowmeter comprising a pair of vortex generator-sensors.

FIG. 9 illustrates another cross section of the embodiment shown in FIG. 8.

FIG. 10 illustrates a cross section of a further embodiment of the mass-volume flowmeter comprising a pair of vortex generator-sensors.

FIG. 11 illustrates a cross section of the vortex generator-sensor included in the embodiment shown in FIG. 10.

Figure 12:
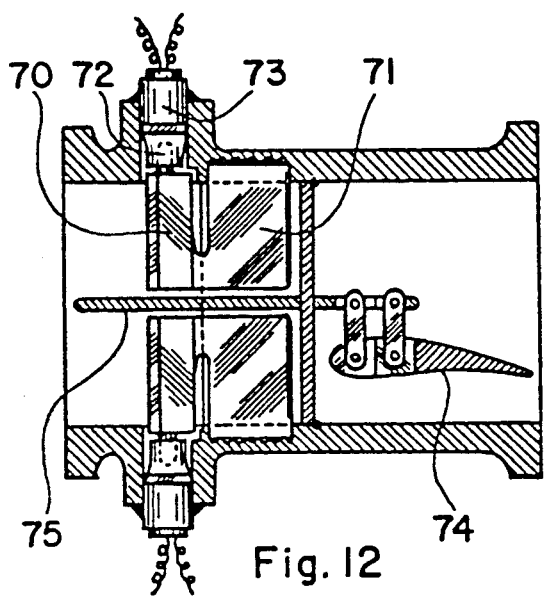
FIG. 12 illustrates a cross section of yet another embodiment of the mass-volume flowmeter comprising a pair of vortex generator-sensors.

In FIG. 1 there is illustrated a cross section of an embodiment of the mass-volume flowmeter constructed in accordance with the principles of the present invention, which flowmeter employs a vortex generator and a pair of vortex sensors. The flowmeter body 1 includes a bore 2 extending from one extremity of the flowmeter body to the other extremity of the flowmeter body 1, which bore 2 is divided into two flow passages 3 and 4 by a divider plate 5. A vortex generating bluff body 6 of an elongated cylindrical shape is disposed across both flow passages 3 and 4 and affixed to the flowmeter body 1, wherein the bluff body 6 extends through the divider plate 5 in a generally leak-proof arrangement. A pair of vortex sensors 7 and 8 are respectively disposed in the two flow passages 3 and 4 at a cross section downstream of the vortex generator 6. Each of the two vortex sensors 7 and 8 comprises a planar member 9 disposed on a plane generally parallel to the plane vortex generator 6 and the central axis of the bore 2, wherein one extremity of the downstream half of the planar member 9 is secured to the flowmeter body, while one extremity of the upstream half of the planar member 9 partially separated from the downstream half by a slit is connected to a force receiving member 9 extending from a transducer container 11. One of the two flow passages 4 includes a flow obstructing member 12 such as a flap shutter disposed in a pivoting relationship about a pivot axis 13, wherein a bias torque keeps the flow obstructing member 12 at the fully closed position whereat the flow passage 4 is completely or substantially closed thereby. The fluid moving through the flowmeter exerts a fluid dynamic force on the flow obstructing body 12, which fluid dynamic force opens up the flow obstructing body 12 wider and wider as the fluid velocity becomes greater and greater. It is quite clear that when the fluid velocity is very small, the fluid will flow only through the flow passage 3 as the flow passage 4 remains fully blocked by the flow obstructing body 12, while equal amounts of fluid flow will occur through the two flow passages 3 and 4 when the fluid velocity becomes very high, wherein the flow obstructing member 6 is deflected to the fully open position (shown in broken lines) by a large fluid dynamic force thereon. It should be noticed that the fluid dynamic force on the flow obstructing body 12 is predominantly a drag force when the fluid velocity is low, while it is predominantly a lift force when the fluid velocity is high.

In FIG. 2 there is illustrated another cross section of the embodiment shown in FIG. 1, which cross section is taken along plane 2—2 as shown in FIG. 1. The flow obstructing member 6 comprises a flap having a semicircular planar shape pivotably supported by a pair of bearings 14 and 15 secured to the flowmeter body 1 in a pivoting relationship about the pivoting axis 13. In this particular arrangement, the bias torque keeping the flap 6 at the fully closed position is provided by the weight of the flap 6. It is readly readily noticed that other bias torque means such as a spring or additional weight may be employed.

In FIG. 3 there is illustrated a cross section of an embodiment of the transducer container 11 included in the embodiment shown in FIG. 1, which cross section is taken along a plane perpendicular to the planar member 9 and perpendicular to the divider plate 5. The transducer container 11 includes a cylindrical cavity therein, which contains a pair of Piezo electric elements 16 and 17 respectively polarized in two opposite directions which are pressed onto a thin end wall of the cylindrical cavity. The thin end wall includes a reinforcing web disposed on a plane perpendicular to the thin wall and intermediate the two Piezo electric elements 16 and 17, from which reinforcing web the force receiving member 10 included in the embodiment shown in FIG. 1 extends. The fluid dynamic force on the planar member 9 shown in FIG. 1 produces lateral deflection of the planar member 9, which in turn exerts stress on the Piezo electric elements 16 and 17 in two opposite directions relative to one another. The electromotive force generated by the two Piezo electric elements 16 and 17 are amplified by a pair of amplifiers 18 and 19 including signal balancing means 20 for cancelling noises generated by mechanical vibrations of the sensor elements therebetween and then combined to obtain an electrical signal 21, representing the fluid dynamic force on the planar member 9.

The two sections of the vortex generating bluff body 6 respectively disposed in the two flow passages 3 and 4 respectively generate two trains of vortices trailing therefrom, wherein the frequency of vortex shedding from each of the two sections of the bluff body is proportional to the fluid velocity moving through the flow passage including that section of the bluff body. The pair of vortex sensors 7 and 8 respectively detect the vortices moving thereby in the two flow passages 3 and 4. Since the fluid velocity U is proportional to the vortex shedding frequency f, the volume flow rate V through the flowmeter is determined by using the following equation:

$$\dot{V} = \frac{S}{2}(U_1 + U_2); U_1 = K_1 f_1 \text{ and } U_2 = K_2 f_2. \quad (1)$$

where S is the total cross sectional area of the flow passages, K is a proportionality constant relating the vortex shedding frequency to the fluid velocity, and the subscripts 1 and 2 respectively stand for the two flow passages 3 and 4. If the divider plate 5 divides the bore 1 into two equal flow passages 3 and 4, $K_1$ and $K_2$ have the same numerical value in the range of the fluid velocity wherein the vortex shedding frequency is linearly proportional to the fluid velocity. Once $K_1$ and $K_2$ are determined empirically by calibrating the flowmeter, the volume flow rate is calculated from equation (1) after substituting the vortex frequencies measured by the vortex sensors 7 and 8 thereinto.

It is evident that the degree of obstruction of the fluid flow through the flow passage 4 created by the flow obstructing member 12 is maximum when the fluid velocity is very low and decreases to a minimum as the fluid velocity increases to a very large value, as the fluid dynamic force opening the flow obstructing flap member 12 is generally proportional to the dynamic pressures of the fluid flowing through the two flow passages 3 and 4. As a consequence, a mathematical relationship of the following form exists between the inequality of the fluid velocity in the two flow passages and the dynamic pressure of the fluid flow:

$$\frac{U_1}{U_2} - 1 = F(A\rho U_1^2 + B\rho U_1 U_2 + C\rho U_2^2), \quad (2)$$

where F stands for a monotonically decreasing function, $\rho$ is the density of the fluid and A, B and C are parametric constants. The inverse relationship of equation (2) provides equation $$\rho(AU_1^2 + BU_1U_2 + CU_2^2) = F^{-1}\left(\frac{U_1'}{U_2} - 1\right), \quad (3)$$

which equation may be rearranged into the following form:

$$\rho U_1^2 = H_1\left(\frac{U_1}{U_2}\right), \quad (4)$$

and $$\rho U_2^2 = H_2\left(\frac{U_1}{U_2}\right), \quad (5)$$

where $H_1$ and $H_2$ stand for functional relationships to be determined empirically. Equations (4) and (5) can be combined to obtain the following equation for the mass flow rate M:

$$\dot{M} = \frac{S}{2}\left[\frac{1}{U_1}H_1\left(\frac{U_1}{U_2}\right) + \frac{1}{U_2}H_2\left(\frac{U_1}{U_2}\right)\right]. \quad (6)$$

Once the functional relationships $H_1$ and $H_2$ are empirically determined by calibrating the flowmeter, the mass flow rate through the flowmeter is calculated from equation (6) after substituting the fluid velocities $U_1$ and $U_2$ respectively determined from the vortex shedding frequencies $f_1$ and $f_2$ measured by the vortex sensors 7 and 8. In summary, the mass-volume flowmeter of the present invention employing a pair of fluid velocity sensors determines the volume flow rate from an additive combination of the outputs from the two flow velocity sensors, and the mass flow rate from an empirically determined relationship equivalent to equation (6). The density of the fluid is readily determined as the ratio of the mass flow rate to the volume flow rate. It should be mentioned that, firstly, the two flow passages 3 and 4 may be provided by two separate conduits in place of the single bore divided by the divider plate and, secondly, the flow obstructing member may employ other shapes than the simple flap shown in the illustrative embodiment.

The filter-amplifier 148 refines the flow signals supplied by the vortex sensors 8 and 9 through noise-rejection and signal amplifying process, and the data processor 149 determines the volume flow rate and/or mass flow rate by executing calculations involved in equations (1) and/or (2) or in empirically determined equations equivalent thereto, which data processor may also determine the density of the fluid as a ratio of the mass flow rate to the volume flow rate. In figures showing other illustrative embodiments which follow, the filter-amplifier and the data processor are not shown for the brevity of the illustration, as those combinations operate on principles and methods similar or parallel to the embodiment shown in FIG. 1.

In FIG. 4 there is another arrangement of the flow obstructing member playing the same role as the element 12 included in the embodiment shown in FIGS. 1 and 2. This version of the flow obstructing member 22 includes a bias torque provided by a mechanical spring 23 in place of or in addition to that provided by the weight of the flap 22, which bias torque keeps the flap 22 at the fully closed position in the absence of the fluid dynamic force. The flow obstructing member 22 may further include an actuator means for fully opening or fully closing the flap 22 in an over-riding mode, which actuator means includes a high pitch screw 24 extending from the pivoting shaft of the flap 22 and engaging a matched high pitch thread included in the nonrotating free sliding block 25, wherein the flap 22 opens fully when the actuator rod 26 extends all the way towards the flowmeter body. The flow obstructing flap member 22 may include a hole 27 that allows a certain minimum amount of fluid flow through the flow passage blocked by the flap 22 even when that flap is fully closed.

In FIG. 5 there is illustrated a cross section of an embodiment of a mass volume flowmeter having essentially the same construction and operating principles as the embodiment shown in FIGS. 1 and 2 with a few exceptions, which are, firstly, the two vortex sensors 28 and 29 are disposed at two different downstream cross sections of the flow passages and, secondly, the vortex generating bluff body 30 extends through an over-sized hole 31 disposed through the divider plate 32, which combination includes a shutter plate 34 actuated by an actuator rod 34 that closes the gap about the sides of the bluff body 30 in the over-sized hole 31 when the actuator rod 34 is pulled away from the flowmeter body. The flow obstructing flap member 35 includes an over-riding actuator mechanism comprising elements 24, 25 and 26 included in the embodiment shown in FIG. 4, which opens the flap 35 to the fully open position when it is actuated.

In FIG. 6 there is illustrated another cross section of the embodiment shown in FIG. 5, which cross section is taken along plane 6—6 as shown in FIG. 5. The shutter plate 36 opens and closes the gap about the sides of the vortex generating bluff body 30 in the over-sized hole 31 when the stiff chord member 36 connected to the actuator rod 34 is pushed toward or pulled away therefrom.

The mass-volume flowmeter shown in FIGS. 5 and 6 and operating on vortex shedding principles operates on the same principles as those described in conjunction with FIGS. 1, 2 and 3 in measuring mass and volume flow rates in which mode of operation the shutter plate 33 is pulled to the fully closed position. This mass-volume flowmeter is capable of measuring the fluid velocity in another mode of operation. When the shutter plate 33 is at the open position providing a gap about the bluff body 30 and the flow obstructing flap member is fully opened by the over-riding actuator, the fluid velocity is the same in the two flow passages and the vortices are shed from the bluff body 30 at the same frequency in unison in both passages. As a consequence, the fluid velocity can be determined from the time interval between the instants of vortex detection by the two vortex sensors 28 and 29. This method of measuring the fluid velocity is useful to supplement or to check the accuracy of the fluid velocity determined from the vortex shedding frequency in low velocity flows where the proportionality relationship between the fluid velocity and the vortex shedding frequency is nonlinear.

In FIG. 7 there is illustrated a cross section of an embodiment of the mass-volume flowmeter employing vortex shedding principles, which embodiment has essentially the same construction and operating principles as the embodiment shown in FIGS. 1 and 2 with one exception in the arrangement of the planar member included in the vortex sensors 37 and 38. The planar member 39 included in each of the two vortex sensors 37 and 38 extends from the reinforcing rib 40 built on the end face of the transducer container 41 in a cantilever arrangement. The flow obstructing flap member 42 has a lift force generating cross section, that provides a smoothly extending configuration as a continuation of the trailing edge of the divider plate 43 even when the flap 42 is at the fully closed position. This type of flap may be employed in place of the flow obstructing flap member shown in FIG. 1 or 5.

In FIG. 8 there is illustrated a cross section of an embodiment of the mass-volume flowmeter that employs a pair of vortex generator-sensors. The bore through the flowmeter body is divided into two flow passages 44 and 45 by a divider plate 46. A pair of vortex generating bluff bodies 47 and 48 respectively extending from the reinforcing ribs of the end faces of the two transducer containers 49 and 50 are disposed across the cross section of the two flow passages 44 and 45, respectively, which bluff bodies also function as vortex sensors. The flow obstructing flap member 51 has an extended leading edge 52 that partially obstructs the flow passage 44 when the flap member 51 is at the fully closed position completely blocking the flow passage 45.

In FIG. 9 there is illustrated another cross section of the embodiment shown in FIG. 8, wheich cross section is taken along plane 9—9 as shown in FIG. 8. The bluff bodies 47 and 48 respectively extend from the reinforcing webs 53 and 54 disposed across the end faces of the transducer containers 49 and 50, respectively. The reduction of the cross section of the bluff body-transducer container assembly at the reinforcing web provides a stress concentration that amplifies the stress exerted on the Piezo electric elements contained in the transducer container by the lateral fluid dynamic force acting on the bluff body. The mass-volume flowmeter shown in FIGS. 8 and 9 operates on the same principles as those described in conjunction with FIGS. 1, 2 and 3.

In FIG. 10 there is illustrated a cross section of an embodiment of the mass-volume flowmeter comprising a pair of vortex generator-sensors 55 and 56 respectively measuring fluid velocities in the two flow passages 57 and 58 included in the flowmeter body. Each of the pair of vortex sensors includes a bluff body 59 with one extremity secured to the flowmeter body and extending across the flow passage, which bluff body has a planar trailing edge extension 60 engaging a groove included in a pressure shielding memeber 61 having a U-shaped cross section that is affixed to the flowmeter body at both extremities thereof. The planar trailing edge extension 60 of the bluff body 59 is partially separated from the bluff body by a slit 62 and a deflective extremity thereof is connected to a force receiving member 63 extending from a transducer container 64. In this embodiment, the flow obstructing member 65 comprises an airfoil section 66 disposed generally parallel to the divider plate 67, that is supported by a rotatable disc 68 in an arrangement wherein the airfoil section 66 maintaining a constant angle of attack relative to the flow direction orbits about the rotation axis 69 of the supporting disc 68. The mechanism maintaining the constant angle of attack for the airfoil section 66 may employ fluid dynamic torque on the airfoil section that is mass balanced about the pitching axis thereof, or a mechanical rotary motion coupling that prevents the pitching movement of the airfoil section 66 while allowing the orbiting movement thereof about the rotation axis 69. This particular arrangement of the flow obstructing member 65 provides an advantage in view that the fluid dynamic force on the airfoil section is dominantly a lift force which varies in a more regular way as a function of the dynamic pressure of the fluid flow.

In FIG. 11 there is illustrated another cross section of the embodiment shown in FIG. 10, which cross section is taken along plane 11—11 as shown in FIG. 10. The bluff body 59 has a planar trailing edge extension 60 engaging a groove included in a planar pressure shielding member 61 in a clearance relationship therebetween. The two side surfaces of the combination of the bluff body 59 and the planar trailing edge extension 60 are exposed to the fluctuating fluid pressures associated with the two rows of vortices shed from two sides of the bluff body in an alternating pattern, respectively.

In FIG. 12 there is illustrated a cross section of an embodiment of the mass-volume flowmeter having a construction similar to the embodiment shown in FIGS. 10 and 11 with a few exceptions, which exceptions include: Firstly, the combination of the bluff body 70 and the planar trailing edge extension 71 is secured to the flowmeter body by a deflective extremity of the planar trailing edge extension affixed to the flowmeter body and one extremity of the bluff body is connected to the force receiving member 72 of the transducer container 73, and, secondly, the flow obstructing member comprises an airfoil section 74 maintaining a constant angle of attack that is disposed in an orbiting arrangement about an orbit axis parallel and adjacent to the trailing edge of the divider plate 75.

Figure 13:
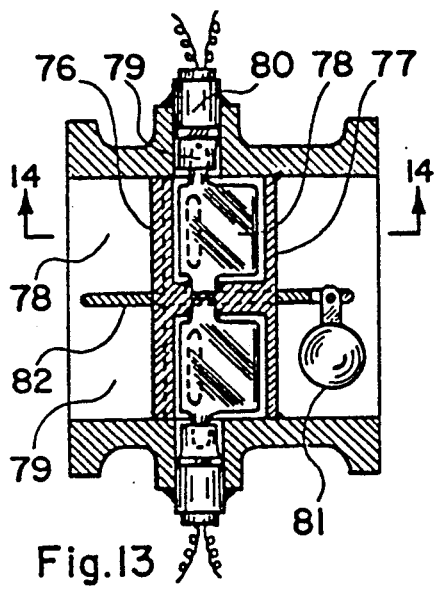
FIG. 13 illustrates a cross section of yet a further embodiment of the mass-volume flowmeter comprising a pair of vortex generator-sensors.

In FIG. 13 there is illustrated a cross section of an embodiment of the mass-volume flowmeter comprising a bluff body 76 with a trailing edge extension 77 that extends across both flow passages 78 and 79. Each of the two half sections of the combination of bluff body and planar trailing edge extension includes a cavity housing a vortex sensing planar member with one extremity connected to the force receiving member 79 of the transducer container 80 and the other extremity secured to the bluff body structure. The flow obstruction member 81 employed in this embodiment comprises a ball disposed in an orbiting relationship about an orbit axis parallel and adjacent to the trailing edge of the divider plate 82, wherein the fluid dynamic force on the flow obstructing member 81 is predominantly a drag force. The planar cavity housing the vortex sensing planar member 78 includes two slotted openings respectively open to the two opposite sides of the combination of the bluff body and the trailing edge extension.

Figure 14:
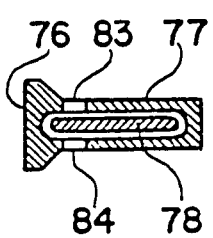
FIG. 14 illustrates a cross section of the vortex generator-sensor included in the embodiment shown in FIG. 13.

In FIG. 14 there is illustrated a cross section of the combination of bluff body and the trailing edge extension included in the embodiment shown in FIG. 13 which cross section taken along plane 14—14 as shown in FIG. 13 clearly shows the two slotted openings respectively disposed through the side walls of the combination of the bluff body 76 and the planar trailing edge 77. The mass-volume flowmeters shown in FIGS. 10, 12 and 13 operate on the same principles as those described in conjunction with FIGS. 1, 2 and 3.

Figure 15:
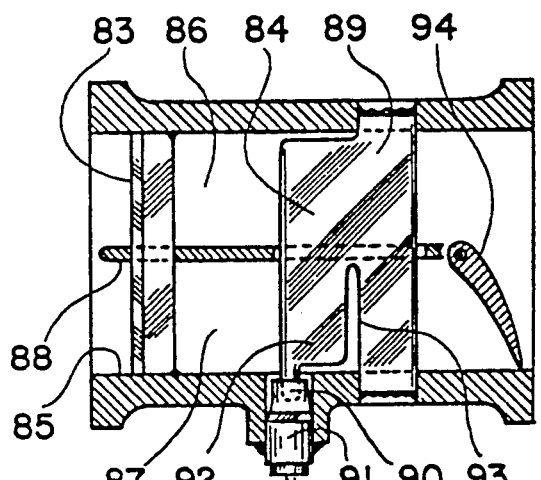
FIG. 15 illustrates a cross section of an embodiment of the mass-volume flowmeter comprising vortex generator and a vortex sensor detecting dual vortex shedding frequencies.

In FIG. 15 there is illustrated a cross section of an embodiment of the mass-volume flowmeter comprising a vortex generating bluff body 83 and a vortex sensing planar member 84 respectively disposed across two different cross sections of the bore 85 divided into two flow passages 86 and 87 by a divider plate 88. The bluff body 83 extends through a zero clearance hole disposed through the divider plate 88 and is secured to the flowmeter body. The vortex sensing planar member 84 extending through a clearance hole disposed through the divider plate 88 is secured to the flowmeter body at least one extremity 89 thereof and connected to the force receiving member 90 of a transducer container 91 at the other extremity 92. In order to enhance the lateral deflection of the vortex sensing planar member 84 under an alternating lateral fluid dynamic force exerted by the vortices moving thereby, the upstream half of the vortex sensing member 84 connected to the force receiving member 90 of the transducer container may be partially separated from the downstream half thereof by a slit 93, which downstream half is now secured to the flowmeter body at both extremities thereof. The flow obstructing member 94 may be a flap as shown in the illustrated embodiment or other designs exemplified by the embodiments shown in FIGS. 10, 12 or 13. The vortex sensor comprising the planar member 84 and the transducer container 91 simultaneously detects two frequencies of vortex shedding respectively taking place in the two flow passages 86 and 87. A signal processor connected to the transducer determines the two vortex shedding frequencies, from which the mass and volume flow rates are determined on the same principles as those described in conjunction with FIGS. 1, 2 and 3.

Figure 16:
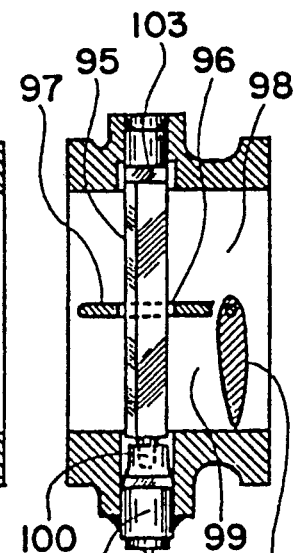
FIG. 16 illustrates a cross section of an embodiment of the mass-volume flowmeter comprising a vortex generator-sensor detecting dual vortex shedding frequencies.

In FIG. 16 there is illustrated a cross section of an embodiment the mass-volume flowmeter comprising a single vortex generator-sensor 95 extending through a hole 96 disposed through the divider plate 97, which bluff body 95 is disposed across both flow passages 98 and 99. There is a small clearance in the hole 96 about the bluff body 95 that allows a lateral deflection of a small magnitude for the bluff body while limiting the leak of fluid therethrough to a negligible amount. One extremity of the bluff body 95 is secured to the flowmeter body, while the other extremity is connected to the force receiving member 100 of the transducer container 101. The flow obstructing member 102 may comprise a flap or other designs exemplified by the embodiments shown in FIGS. 10, 12 and 13. In order to enhance the lateral deflection of the bluff body without increasing the resonance frequency thereof, the extremity of the bluff body secured to the flowmeter may include a section 103 of thin cross section and the bluff body may have a hollow core. The mass flowmeter shown in FIG. 16 operates on the same principles as those of the embodiment shown in FIG. 15.

Figure 17:
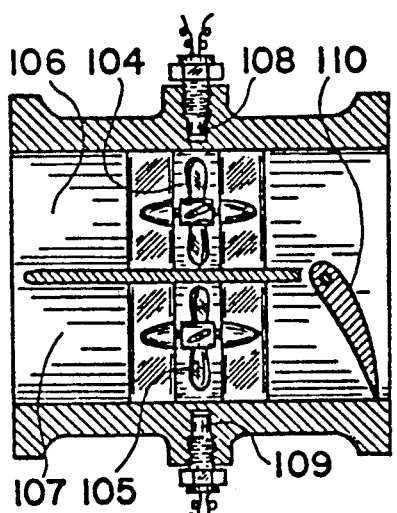
FIG. 17 illustrates a cross section of an embodiment of the mass-volume flowmeter comprising a pair of turbines.

In FIG. 17 there is illustrated a cross section of an embodiment of the mass-volume flowmeter comprising a pair of turbine type fluid velocity sensors 104 and 105 respectively disposed in two flow passages 106 and 107. The pair of transducers respectively detecting the rotary speeds of the two turbines provide frequency signals proportional to the fluid velocities in the two flow passages 106 and 107. The flow obstructing member 110 may be one of many different designs previously described. The mass-volume flowmeter shown in FIG. 17 determines the volume and mass flow rates on the same principles described in conjunction with equations (1) and (6), wherein f now stands for the frequency of rotation of the turbine proportional to the fluid velocity instead of the vortex shedding frequency.

Figure 18:
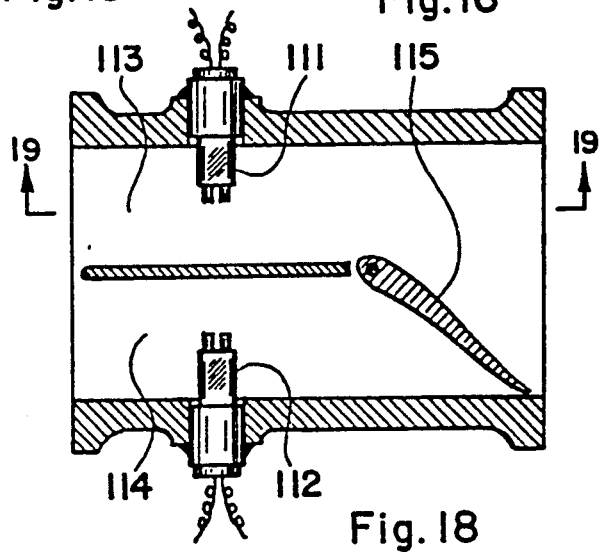
FIG. 18 illustrates a cross section of an embodiment of the mass-volume flowmeter comprising a pair of thermal flow sensors.

In FIG. 18 there is illustrated a cross section of an embodiment of the mass-volume flowmeter comprising a pair of thermal flow sensors 111 and 112 respectively disposed in two flow passages 113 and 114. A flow obstructing member 115 obstructs at least one of the two flow passages at degrees progressively decreasing with the increasing flow rate through the flowmeter.

Figure 19:
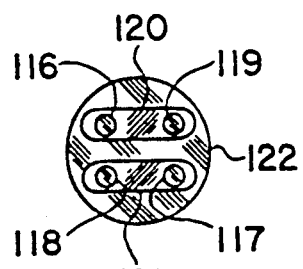
FIG. 19 illustrates a cross section of the thermal flow sensor included in the embodiment shown in FIG. 18.

In FIG. 19 there is illustrated an end view of the thermal flow sensors included in the embodiment shown in FIG. 18, which end view is taken through plane 19—19 as shown in FIG. 18. Each of the thermal flow sensors 111 and 112 comprises two heated temperature probes 116 and 117 and two ambient temperature probes 118 and 119, in which combination one pair of the thermal probes 116 and 119 are supported by a first slender support member 120, while the other pair of the thermal probes 117 and 118 are supported by a second slender support member 121, which support members are anchored to a circular cylindrical base 122 secured to the flowmeter body and extending into the flow passage.

The mass flow rate is determined from the difference in the temperature between the first pair of thermal probes 116 and 119 and that between the second pair of thermal probes 117 and 118. The mass flow rate is through the flowmeter is given by equation $$\dot{M} = \frac{S}{2}(\rho U_1 + \rho U_2), \quad (7)$$

where S is the total cross sectional area of the flow passages and $\rho U_1$ and $\rho U_2$ are respectively measured by the thermal flow sensors 111 and 112. Equations (4) and (5) can be combined to obtain the following equation for the volume flow rate V:

$$\dot{V} = \frac{S}{2}\left[\frac{1}{\rho U_1} H_1\left(\frac{\rho U_1}{\rho U_2}\right) + \frac{1}{U_2} H_2\left(\frac{\rho U_1}{\rho U_2}\right)\right]. \quad (8)$$

Once the functional relationship $H_1$ and $H_2$ are empirically determined by calibrating the flowmeter, the mass flow rate through the flowmeter is canculated from equation (8) after substituting the mass flux densities $\rho U_1$ and $\rho U_2$ respectively measured by the two thermal flow sensors. In summary, the mass-volume flowmeter of the present invention employing a pair of mass flux density measuring sensors determines the mass flow rate from an additive combination of the outputs from the two mass flow measuring sensors, and the volume flow rate from an empirically determined relationship given by equation (8). The density of the fluid is readily determined as the ratio of the mass flow rate to the volume flow rate.

Figure 20:
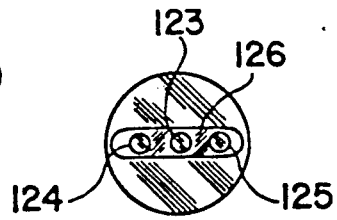
FIG. 20 illustrates a cross section of an alternative thermal flow sensor usable in place of the embodiment shown in FIG. 19.

In FIG. 20 there is illustrated an end view of another embodiment of the thermal flow sensor comprising three temperature probes, which can be used in place of the embodiment shown in FIG. 19 in constructing the mass-volume flowmeter illustrated in FIG. 18. This embodiment of the thermal flow sensors comprises a heated temperature probe 123 disposed intermediate two ambient temperature probes 124 and 125, which combinations are supported by a single slender support member 126 extending into the flow passage. The mass flux density $\rho U$ is determined from the difference in temperature between the ambient temperature probes 124 and 125. It should be mentioned that the thermal flow sensors shown in FIGS. 19 and 20 are only illustrative examples which can be employed in the construction of the mass-volume flowmeter of the present invention. Other types of thermal flow sensors comprising two or single thermal probes used in the existing arts of measuring mass flow rate may be employed in place of those shown in the illustrative embodiments.

Figure 21:
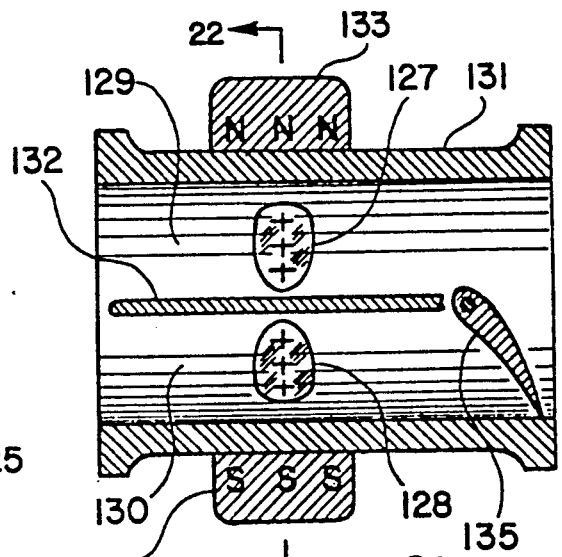
FIG. 21 illustrates a cross section of an embodiment of the mass-volume flowmeter comprising a pair of electromagnetic flow sensors.

In FIG. 21 there is illustrated a cross section of an embodiment of the mass-volume flowmeter comprising a pair of electromagnetic flow sensors 127 and 128 respectively disposed in two flow passages 129 and 130. The conduit 131 divided into the two flow passages 129 and 130 by the divider plate 132 is disposed intermediate a pair of magnetic poles 133 and 134 having opposite polarities to one another, which magnetic poles provide a magnetic field generally perpendicular to the divider plate 132 and extending across both flow passages. The flow obstructing member 135 obstructs at least one of the two flow passages at degrees varying with the flow rates through the flowmeter.

Figure 22:
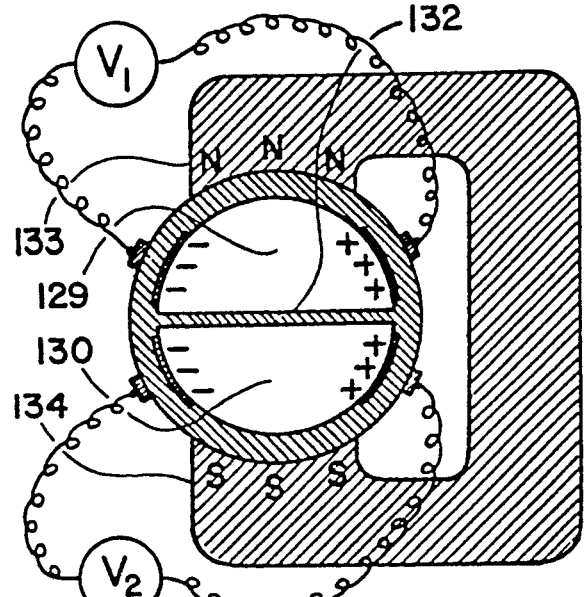
FIG. 22 illustrates another cross section of the embodiment shown in FIG. 21.

In FIG. 22 there is illustrated another cross section of the embodiment shown in FIG. 21, which cross section is taken along plane 22—22 as shown in FIG. 21. The fluid with an electric conductivity flowing through the flow passages 129 and 130 generates electromotive force $V_1$ and $V_2$ across the pair of electrodes included in each of the two electromagnetic probes 127 and 128, respectively, which emf $V_1$ and $V_2$ is respectively proportional to the fluid velocity $U_1$ and $U_2$ in the two flow passages. The volume and mass flow rate are respectively determined by equations (1) and (6).

Figure 23:
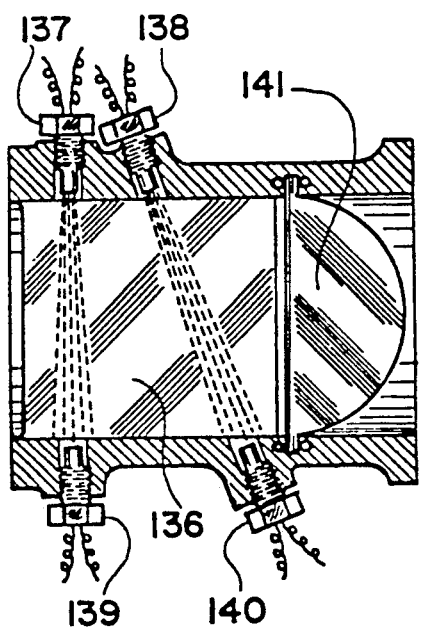
FIG. 23 illustrates a cross section of an embodiment of the mass-volume flowmeter comprising a pair of acoustic flow sensors.

In FIG. 23 there is illustrated a cross section of an embodiment of the mass-volume flowmeter comprising a pair of acoustic flow sensors respectively disposed in two flow passages separated from one another by a divider plate 136, which cross section is taken along a plane including the divider plate 136. Each of the two flow passages includes a pair of ultrasonic emitters 137 and 138 and a pair of ultrasonic detectors 139 and 140. The combination of the elements 137 and 139 measures the speed of acoustic wave propagation in a direction perpendicular to the flow direction, while the combination of the elements 138 and 140 measures the speed of acoustic wave propagation in a direction oblique to the flow direction. The difference in the speed of acoustic wave propagation in those two directions is proportional to the fluid velocity. Once the fluid velocities in the two flow passages are determined from the information provided by the acoustic flow sensors, the volume and mass flow rates are determined from equations (1) and (6). An acoustic flow sensor measuring the fluid velocity in each of the two flow passages may include a pair of ultrasonic emitters-detectors disposed in place of the elements 138 and 140. The difference in the speed of acoustic wave propagation from the element 138 to 140 and that from 140 to 138 is proportional to the fluid velocity in the flow passage. In such an arrangement, the need for elements 137 and 139 is eliminated. As a futther alternative, an acoustic flow sensor comprising a wide angle ultrasonic emitter disposed in place of the two emitters 137 and 138 may be employed in conjunction with the pair of detectors 139 and 140. The Doppler type acoustic flow sensors may be employed in place of the acoustic flow sensors described in conjunction with the embodiment shown in FIG. 23. The flow obstructing member 141 may be of one of many different designs shown in the preceding illustrative examples.

Figure 24:
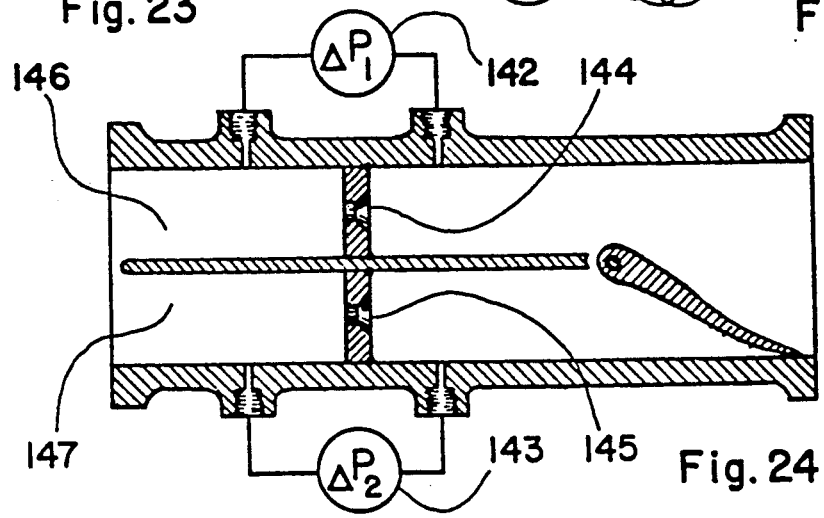
FIG. 24 illustrates a cross section of an embodiment of the mass-volume flowmeter comprising a pair of differential pressure sensors respectively in conjunction with a pair of flow passage constrictions.

In FIG. 24 there is illustrated a cross section of an embodiment of the mass-volume flowmeter comprising a pair of differential pressure flow sensors 142 and 143 respectively measuring pressure drops across two orifices 144 and 145 disposed in the two flow passages 146 and 147, respectively. The pressure drop $\Delta P$ in each of the two flow passages is proportional to the dynamic pressure of the fluid flow in that flow passage.

$$\frac{1}{2}\rho U_1^2 = G_1 \Delta P_1 \text{ and } \frac{1}{2}\rho U_2^2 = G_2 \Delta P_2, \quad (9)$$

where $G_1$ and $G_2$ are parametric coefficient determined empirically by calibrating the flowmeter. When the differential pressure is measured in terms of the differential height $\Delta h$ of a manometric column of the fluid moving through the flowmeter, equation (9) can be written in the form:

$$U_1 = \sqrt{2G_1 g \Delta h_1} \text{ and } U_2 = \sqrt{2G_2 g \Delta h_2}, \quad (10)$$

where g is the gravitational acceleration of the earth. Substitution of the fluid velocities $U_1$ and $U_2$ measured by the manometric differential pressure gauges per equation (9) into equations (1) and (6) provides the volume and mass flow rates.

It should be understood that the flow obstruction member blocking one of the two flow passages included in the mass-volume flowmeter of the present invention may employ many other designs optimized to provide the best repeatability in the performance of the flowmeter, which designs must be decided by experimental process. The two flow passages included in the mass-volume flowmeter may comprise a common bore through the flowmeter body divided into two equal halves by a divider plate or two separate conduits. The functional relationship relating the velocity ratio $U_1/U_2$ to the volume or mass flow rate given by equations (6) or (7) may be replaced by other functional relationships determined by experimental process, which may employ $(U_1-U_2)$ or $(U_1-U_2)/(U_1+U_2)$ as an independent variable instead of $U_1/U_2$.

While the principles of the present inventions have now been made clear by the illustrative embodiments, there will be many obvious modifications in the structures, arrangements, proportions, elements and materials, which are particularly adapted to the specific working environments and operating conditions in the practice of the invention without departing from those principles. It is not desired to limit the inventions to the particular embodiments shown and described and, accordingly, all suitable modifications and equivalents may be resorted to falling within the scope of the inventions as defined by the claims which follow.

The embodiments of the invention, in which an exclusive property and priviledge is claimed, are defined as follows:

1. A method for measuring flow rate of fluid comprising in combination:
   a) bifurcating a fluid flow to be measured into flow streams respectively moving through two flow passages;
   b) at least partially obstructing at least one of said two flow passages by a flow obstructing member experiencing fluid dynamic force of the fluid flow, said flow obstructing member including a bias force tending to increase the degree of obstruction of the fluid flow through said at least one of the two flow passages, wherein the fluid dynamic force experienced by said flow obstructing member tends to decrease the degree of obstruction of the fluid flow through said at least one of the two flow passages;
   c) obtaining a first signal representing volume flow rate of the fluid moving through one of the two flow passages, and a second signal representing the volume flow rate of the fluid moving through the other of the two flow passages; and
   d) determining mass flow rate of the fluid moving through the two flow passages as a function of said first and second signals and ratio between said signals.

2. The method as set forth in claim 1 wherein volume flow rate of the fluid moving through the two flow passages is determined from an additive combination of said first and second signals.

3. The method as set forth in claim 2 wherein the density of the fluid is determined as a ratio of the mass flow rate to the volume flow rate.

4. A method for measuring flow rate of fluid comprising in combination:
   a) bifurcating a fluid flow to be measured into two flow streams respectively moving through two flow passages;
   b) at least partially obstructing at least one of said two flow passages by a flow obstructing member experiencing fluid dynamic force of the fluid flow, said flow obstructing member including a bias force tending to increase the degree of obstruction of the fluid flow through said at least one of the two flow passages, wherein the fluid dynamic force experienced by said flow obstructing member tends to decrease the degree of obstruction of the fluid flow through said at least one of the two flow passages;
   c) obtaining a first signal representing mass flow rate of the fluid moving through one of the two flow passages, and a second signal representing mass flow rate of the fluid moving through the other of the two flow passages; and
   d) determining volume flow rate of the fluid moving through the two flow passages as a function of said first and second signals and ratio between said signals.

5. The method as set forth in claim 4 wherein mass flow rate of the fluid moving through the two flow passages is determined from an additive combination of said first and second signals.

6. The method as set forth in claim 5 wherein the density of the fluid is determined as a ratio of the mass flow rate to the volume flow rate.

7. An apparatus for measuring flow rate of fluid comprising in combination:
   a) a body including a first and second flow passages;
   b) a flow obstructing member at least partially obstructing at least one of said first and second flow passages, said flow obstructing member including a bias force means tending to increase the degree of obstruction of the fluid flow through said at least one flow passage, wherein fluid dynamic force exerted on said flow obstructing member by the fluid moving through said apparatus tends to decrease the degree of obstruction of the fluid flow through said at least one flow passage;
   c) means for obtaining first signal representing volume flow rate of the fluid moving through said first flow passage, and a second signal representing volume flow rate of the fluid moving through said second flow passage; and
   d) means for determining mass flow rate of the fluid moving through said apparatus as a function of said first and second signals and ratio between said first and second signals.

8. The combination as set forth in claim 7 wherein volume flow rate of the fluid moving through said apparatus is determined from an additive combination of said first and second signals.

9. The combination as set forth in claim 8 wherein the density of the fluid is determined as a ratio of the mass flow rate to the volume flow rate.

10. The combination as set forth in claim 8 wherein said means for obtaining said first and second signals comprises two combinations of a vortex generator and sensor respectively disposed in said first and second flow passages and providing vortex shedding frequencies in said first and second flow passages as said first and second signals.

11. The combination as set forth in claim 8 wherein said means for obtaining said first and second signals comprises a combination of a vortex generator and sensor extending across said first and second flow passages and providing vortex shedding frequencies in said first and second flow passages as said first and second signals.

12. The combination as set forth in claim 8 wherein said means for obtaining said first and second signals comprises two turbines respectively disposed in said first and second flow passages and providing speed of rotation of said turbines as said first and second signals.

13. The combination as set forth in claim 8 wherein said means for obtaining said first and second signals comprises a magnet providing a magnetic field across said first and second flow passages; and means for measuring first electromotive force induced in a direction generally perpendicular to the magnetic field and the fluid velocity generated by the fluid moving through said first flow passage as said first signal, and second electromotive force induced in a direction generally perpendicular to the magnetic field and the fluid velocity generated by the fluid moving through said second flow passage as said second signal.

14. The combination as set forth in claim 8 wherein said means for obtaining said first and second signals comprises two combinations of an acoustic transmitter and receiver respectively included in said first and second flow passages and providing information on the velocity of the fluid moving through said first and second flow passages as said first and second signals.

15. An apparatus for measuring flow rate of fluid comprising in combination:
   a) a body including a first and second flow passages;
   b) a flow obstructing member at least partially obstructing at least one of said first and second flow passages, said flow obstructing member including a bias force means tending to increase the degree of obstruction of the fluid flow through said at least one flow passage, wherein fluid dynamic force exerted on said flow obstructing member by the fluid moving through said apparatus tends to decrease the degree of obstruction of the fluid flow through said at least one flow passage;
   c) means for obtaining first signal representing mass flow rate of the fluid moving through said first flow passage, and a second signal representing mass flow rate of the fluid moving through said second flow passage; and
   d) means for determining volume flow rate of the fluid moving through said apparatus as a function of said first and second signals and ratio between said first and second signals.

16. The combination as set forth in claim 15 wherein mass flow rate of the fluid moving through said apparatus is determined from an additive combination of said first and second signals.

17. The combination as set forth in claim 16 wherein the density of the fluid is determined as a ratio of the mass flow rate to the volume flow rate.

18. The combination as set forth in claim 16 wherein said means for obtaining said first and second signal comprises two convective heat transfer sensors respectively disposed in said first and second flow passages and providing rate of convective heat transfer as a measure of mass flow rate of the fluid flow through said first and second flow passages as said first and second signals.

* * * * *